United States Patent [19]

DeSenna

[11] Patent Number: 5,817,337
[45] Date of Patent: Oct. 6, 1998

[54] DISINFECTANT EFFERVESCENT TABLET FORMULATION

[76] Inventor: Richard A. DeSenna, 2215 Mainsail Dr., NE., Marietta, Ga.

[21] Appl. No.: 561,794

[22] Filed: Mar. 11, 1996

Related U.S. Application Data

[63] Continuation-in-part of Ser. No. 539,875, Oct. 6, 1995, Pat. No. 5,741,520.

[51] Int. Cl.$^6$ ............................................. A61K 9/46
[52] U.S. Cl. ................................................. 424/466
[58] Field of Search ................................. 424/466

[56] References Cited

U.S. PATENT DOCUMENTS

| | | | |
|---|---|---|---|
| 4,252,664 | 2/1981 | Inamorato | 252/99 |
| 4,536,389 | 8/1985 | White et al. | 424/44 |
| 4,618,444 | 10/1986 | Hudson et al. | 252/92 |

*Primary Examiner*—Thurman K. Page
*Assistant Examiner*—James M. Spear
*Attorney, Agent, or Firm*—James W. Kayden; Thomas, Kayden, Horstmeyer, & Risley

[57] ABSTRACT

A water soluble effervescent tablet formulation for preparing a disinfecting solution comprising a first tablet containing a bromide releasing agent and a second tablet containing a hypochlorite releasing agent.

15 Claims, 2 Drawing Sheets

Comparison of Biocidal Activities
HOBr and HOCl

DISINFECTANT EFFERVESCENT TABLET FORMULATION

This is a continuation-in-part of application Ser. No. 08/539,873, filed Oct. 6, 1995, U.S. Pat. No. 5,741,520.

FIELD OF THE INVENTION

The present invention relates generally to a method of cleaning dental and medical instruments, equipment, and the like. More specifically, the invention relates to an effervescent tablet formulation that can be used to prepare a disinfecting solution useful for disinfecting inanimate surfaces.

BACKGROUND OF THE INVENTION

In the medical and dental fields, walls, floors, examination chairs and tables, other equipment, and instruments used in examination and treatment are contaminated by various organic materials which contain or support the growth of various microorganisms. Cleaning alone is not sufficient to kill or inhibit the growth of these organisms and use of disinfectants is necessary.

A disinfectant is a substance which destroys or irreversibly inactivates infectious or other undesirable bacteria, pathogenic fungi, and viruses on surfaces or inanimate objects. Disinfectants kill the growing forms but not necessarily the resistant spore forms of microorganisms. Sterilizers, on the other hand, destroy the growing and spore forms of viruses, bacteria, and fungi on inanimate surfaces. Sanitizers are used to reduce the number of living bacteria or viable virus particles on inanimate surfaces, in water, or in the air, and fungicides and fungistats are used to inhibit the growth of or destroy fungi on inanimate surfaces.

It has become common practice to use glutaraldehyde solutions as surface disinfectants or sterilants in dental and medical facilities. However, while glutaraldehyde solutions are an effective disinfectant, there are many drawbacks to the use of glutaraldehyde, including safety concerns, problems with storing the large volumes of solutions required, and the limited shelf stability of solutions. In addition, if the glutaraldehyde solution is prepared by dilution of a concentrated solution there is the inconvenience of measuring and pouring the liquid concentrate.

The use of disinfectant or sterilant concentrates in a powdered form has been taught in the prior art; for example, in U.S. Pat. No. 5,350,563 to Kralovic et al. The problem with the use of powders as disinfectant concentrates is that they also must be measured in order to prepare the diluted solution and must be poured from one container to another. In addition, there are sometimes problems with forcing the powder into solution.

Another problem faced when using liquid or powdered concentrates is that many of the ingredients used for disinfectants can be harmful to humans and the handling of concentrated amounts of these ingredients can be even more harmful. Care must be taken not to spill or come into contact with any concentrate and not to inhale any dust from powdered concentrates.

Other patents, for example, those of Hunt et al., U.S. Pat. No. 4,265,847, and White et al., U.S. Pat. No. 4,536,389, teach effervescent tablets useful for preparing solutions for sterilizing or disinfecting. Such compositions are rapid water soluble tablets typically comprising an active chemical compound, an alkali metal bicarbonate, e.g. sodium or potassium bicarbonate, and a solid aliphatic carboxylic acid such as citric acid, tartaric acid, adipic acid, or an acid salt thereof. In use, such tablets are dissolved in water whereupon the interaction of the bicarbonate and acid components results in the release of carbon dioxide, thus increasing the rate of solution of the other components and producing a solution in which the active (disinfecting) ingredient is homogeneously dissolved. Methods for forming effervescent tablets are well known in the art. For example, see U.S. Pat. No. 4,265,847 to Hunt et al. and U.S. Pat. No. 5,114,647 to Levesque et al., which disclosures are incorporated herein in their entireties, by reference.

Halogen compounds are effective as disinfecting agents but their use as such agents is limited due to difficulties in storage, mixing, and handling of concentrated halogens and instability of dilute forms. The use of sodium dichloroisocyanurate as a disinfecting agent is known in the prior art. For example, see U.S. Pat. No. 4,536,389, to White et al., and U.S. Pat. No. 5,114,647, to Levesque et al.. Sodium dichloroisocyanurate hydrolyses in water to produce hypochlorous acid (HOCl) and hypochlorite ($OCl^-$), which exist in solution at an equilibrium that is dependent upon the pH of the solution. For example, as shown in FIG. 1, at neutral pH a solution consists of about 75% hypochlorous acid and 25% hypochlorite. The prior art teaches the use of bromide as a disinfectant, the hypobromous acid and hypobromite species are produced in solution typically by the use of bromo, chloro-5,5-dimethylhydantoin. The hypohalous acid specie is the antimicrobial form of the above compounds, with the hypohalite having some antimicrobial effect. However, the negative charge of the hypohalite inhibits its diffusion through the cell wall of microorganisms and thus lowers its antimicrobial effect.

Chloride and bromide have different equilibriums in solution, as shown by the chart of FIG. 1. The dissociation characteristics of hypobromous acid are such that the hypobromous acid is the predominant species over hypobromite up to a pH of about 8.3, which is the point when the concentrations of hypobromous acid and hypobromite are about equivalent. However, hypochlorous acid is a predominant species over hypochlorite only up until a pH of about 7.4. At a pH above about 6.0, as shown by FIG. 1, a solution of hypobromous acid is a much more effective disinfectant because more of the hypohalous species is present. Furthermore, in addition to the greater percentage of hypobromous acid compared to hypobromite, hypobromous acid is a stronger antimicrobial agent than hypochlorous acid, as shown by FIG. 2.

Accordingly, there is a need for an effective disinfecting agent packaged and supplied in a convenient effervescent form. The effervescent tablet must fully dissolve in a rapid fashion to form a homogeneous disinfecting solution which is highly active and stable for a useful length of time.

SUMMARY OF THE INVENTION

It is an object of the present invention to provide an effervescent tablet formulation that can be used to prepare a disinfecting solution wherein the formulation avoids the disadvantages and problems of prior art disinfectant concentrates.

It is an object of the present invention to provide a product to be used for preparing a solution for disinfecting dental and medical instruments and equipment that dissolves fully and results in a solution which has disinfecting power for a useful period of time over a wide pH range.

The present invention comprises a water soluble effervescent tablet formulation that can be added directly to water to prepare a disinfecting solution. The preferred disinfecting agent is a combination of a bromide releasing agent and a hypochlorite releasing agent. Further, the formulation includes a stabilizer for increasing the stability of the effective disinfecting species in solution. In particular, a two tablet system has been developed wherein the bromide releasing agent is in one effervescent tablet and the hypochlorite releasing agent is in a second effervescent tablet.

Sodium bromide is useful as the bromide releasing agent. Sodium dichloroisocyanurate is useful to provide both hypochlorite and to act as a stabilizing agent to maintain desired levels of the active ingredients. Both tablets contain effervescent agents such as are used in the art; for example, sodium bicarbonate in combination with citric acid. Other ingredients may optionally be included such as surfactants, deodorants, lubricants, and fillers.

The tablets prepared from the active agents and the effervescent agents are of such a size and concentration to allow using whole tablets or multiple tablets in a one quart volume or other typically used volume. The use of tablets eliminates having to dilute and mix concentrates, and store diluted liquids. The use of tablets further eliminates having to pour powder concentrates which may produce undesirable and harmful dust. The effervescence provides rapid solubility and mixing of the active ingredients. The use of the two tablet system allows for formation of the preferred hypobromous acid species.

Other objects, features, and advantages of the present invention will become apparent from the following detailed description in conjunction with the accompanying drawings.

DETAILED DESCRIPTION OF PREFERRED EMBODIMENTS

Figure 1:
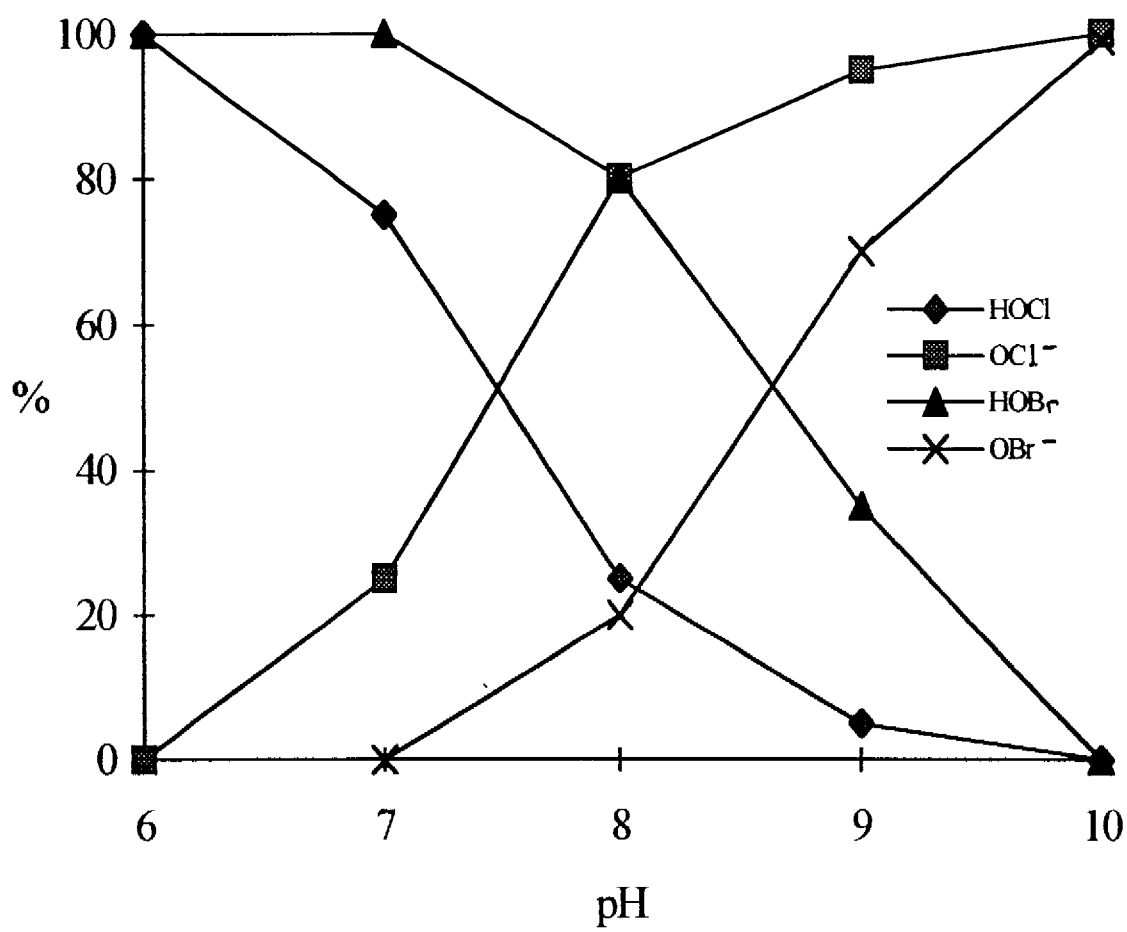
FIG. 1 is a graph showing the dissociation of hypobromous acid and hypochlorous acid.
Figure 2:
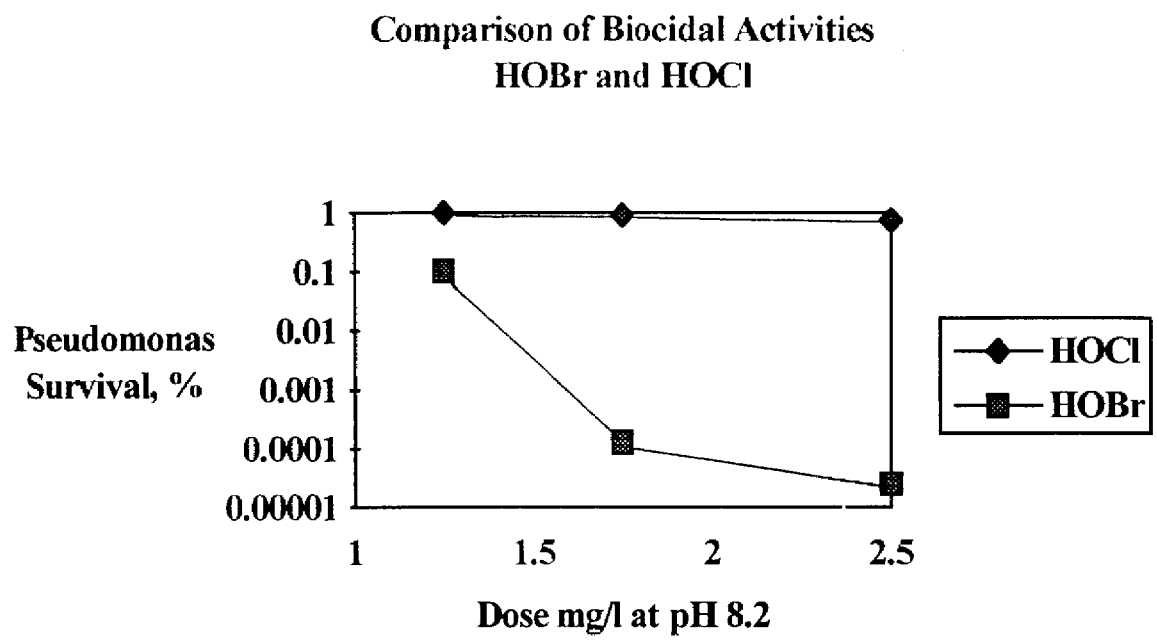
FIG. 2 is a graph comparing the biocidal activities of hypobromous acid and hypochlorous acid.

The present invention is a two tablet effervescent tablet formulation. The tablets are made of appropriate sizes so that, preferably, one of each of the two tablets can be used for one quart of water. In this way a disinfecting solution can be made up as it is needed and does not need to made up in large quantities all at once. Therefore, storage problems are avoided. The use of the effervescent tablets instead of a concentrated liquid or concentrated powder allows for easy handling and mixing of the desired quantity of disinfecting solution.

One tablet, Tablet A, comprises a functional amount of effervescing agent and a bromide releasing agent. The preferred bromide releasing agent is sodium bromide (NaBr). However, other bromide releasing agents may be used, such as, for example, dibromo-dimethylhydantoin, chloro, bromo-dimethylhydantoin, and other bromide salts. The tablet further includes lubricating agents such as, for example, sodium laurel sulfate and PEG 8000, and a filler such as sodium carbonate (soda ash). Tablet B comprises an effective amount of effervescing agent and a hypochlorite releasing agent such as sodium dichloroisocyanurate. It is anticipated that other hypochlorite generating agents can be used such as, for example, lithium hypochlorite, calcium hypochlorite, magnesium hypochlorite, and trichlorisocyanurate. Tablet B further can include a filler such as soda ash and lubricating agents such as sodium laurel sulfate and PEG 8000.

The two tablet formulation avoids reaction between bromide and hypochlorite which would occur if the two chemicals were packaged into one effervescent tablet. The inventor has found that if a bromide releasing agent and hypochlorite releasing agent are combined in a single effervescent tablet, the chemicals will react if the tablet is exposed to a small amount of moisture. Thus, such tablets are not stable.

When one each of Tablets A and B are dissolved in water, sodium dichloroisocyanurate hydrolyses into an equilibrium mix of hypochlorous acid and hypochlorite. Tablet B dissolves and renders free bromide (Br$^-$) and NaBr. The hypochlorite oxidizes the Br$^-$ so that hypobromite is formed. This species in turn forms hypobromous acid so that an equilibrium, dependent upon the pH, is achieved between hypobromite and hypobromous acid.

Effervescent tablet preparation is known in the art. A technique which has worked for the present invention is as follows. Effervescent granules are prepared by mixing 200 kilogram batches of 52.5% sodium bicarbonate, 41.5% citric acid, and 5.5% maltodextrin. This mixture of solids is combined with 20 liters of isopropanol and 800 milliliters of distilled water to form a very dry agglomeration. The agglomeration is dried and coarsely ground into effervescing granules. The effervescing granules are mixed with the other ingredients of Tablet A and Tablet B as described above. In one particular formulation the following amounts of ingredients were used.

| Ingredient | Weight Percent |
| --- | --- |
| TABLET A: | |
| effervescent granules | 66.0 |
| sodium bromide | 10.0 |
| sodium lauryl sulfate | 1.0 |
| soda ash | 20.0 |
| PEG 8000 | 3.0 |
| Total = | 100.0 |
| TABLET B: | |
| effervescent granules | 47.0 |
| sodium dichloroisocyanurate | 24.0 |
| soda ash | 25.0 |
| sodium lauryl sulfate | 1.0 |
| PEG 8000 | 3.0 |
| Total = | 100.0 |

The above mixtures of ingredients were blended and then formed into tablets on an 18 station tablet press. Each tablet contained about 3 grams.

One of each of the above tablets is added to about one quart of water at room temperature and allowed to completely solubilize. The solution can be applied to the area to be cleaned with a spray bottle, cloth, sponge, mop, or other cleaning method.

Another technique for effervescent tablet preparation which is useful for the present invention is as follows. The below listed ingredients were blended and then formed into tablets on an 18 station tablet press. Each tablet contained about 3 grams. In this formulation effervescent granules do not need to be prepared but rather the effervescing agents are directly mixed with the other ingredients. This formula provides a tighter and firmer tablet and is also less expensive.

| Ingredient | Weight Percent |
|---|---|
| TABLET A: | |
| sodium bicarbonate | 31.5 |
| citric acid | 23.3 |
| soda ash | 22.8 |
| sodium bromide | 10.0 |
| sorbitol | 7.4 |
| sodium lauryl sulfate | 1.0 |
| carbowax 8000 | 3.0 |
| sodium benzoate | 1.0 |
| Total = | 100.0 |
| TABLET B: | |
| sodium bicarbonate | 25.0 |
| citric acid | 18.3 |
| soda ash | 21.7 |
| sodium dichloroisocyanurate | 24.7 |
| sorbitol | 5.3 |
| sodium lauryl sulfate | 1.0 |
| carbowax 8000 | 3.0 |
| sodium benzoate | 1.0 |
| Total = | 100.0 |

The weight percentages of the above ingredients can be altered and the tablet sizes can be altered as long as an effective pH and concentration of halogen are present in the prepared solution. An effective pH for a disinfecting solution is from about 6.5–7.5. The pH of the solution prepared as above is about 7.2. An effective concentration of halogen in the prepared solution is from about 300–550 ppm. A preferred concentration is from about 375–440 ppm. A solution prepared as above has about 400 ppm halogen.

It can be appreciated by those skilled in the art that a novel disinfecting product and modifications thereof have been shown and described in detail herein. Various additional changes and modifications may be made without departing from the scope of the present invention.

What is claimed is:

1. An effervescent tablet formulation for preparing a disinfecting solution, comprising:
    a first tablet comprising an effervescing agent, a bromide releasing agent, a lubricating agent and a filler; and
    a second tablet comprising an effervescing agent and a hypochlorite releasing agent.

2. A tablet formulation for preparing a disinfecting solution, comprising:
    a first effervescing tablet comprising an agent that releases bromide upon dissolution of the tablet in aqueous solution;
    a second effervescing tablet comprising an agent that releases hypochlorite upon dissolution of the tablet in aqueous solution; and
    a lubricating agent in at least one of said first and second effervescing tablets.

3. An effervescent tablet formulation for preparing a disinfecting solution, comprising:
    a first tablet comprising an effervescing agent and a bromide releasing agent; and
    a second tablet comprising an effervescing agent, a hypochlorite releasing agent, a lubricating agent and a filler.

4. The effervescent tablet formulation of claim 1, wherein said bromide releasing agent includes sodium bromide.

5. The effervescent tablet formulation of claim 1, wherein said hypochlorite releasing agent is selected from the group consisting of sodium dichloroisocyanurate, sodium trichloroisocyanurate, lithium hypochlorite, calcium hypochlorite, and magnesium hypochlorite.

6. The effervescent tablet formulation of claim 1, wherein said hypochlorite releasing agent includes sodium dichloroisocyanurate.

7. The effervescent tablet formulation of claim 1, wherein said effervescent agent includes a mixture of sodium bicarbonate and citric acid.

8. An effervescent tablet formulation for preparing a disinfecting solution, comprising:
    a first tablet comprising an effervescing agent and a bromide releasing agent; and
    a second tablet comprising an effervescing agent and a hypochlorite releasing agent;
    wherein said effervescing agent includes granules formed from a mixture of about 52.5% sodium bicarbonate, about 44.5% citric acid, and about 5.5% maltodextrin, and in which wetting agents isopropanol and distilled water are used to agglomerate said mixture and the agglomerated mixture is formed into granules.

9. An effervescent tablet formulation for preparing a disinfecting solution, comprising:
    a first tablet comprising an effervescing agent, a bromide releasing agent, a lubricating agent and a filler, said lubricating agent comprising a combination of sodium lauryl sulfate and PEG 8000 and said filler comprising sodium carbonate; and
    a second tablet comprising an effervescing agent and a hypochlorite releasing agent.

10. The effervescent tablet formulation of claim 3, wherein said bromide releasing agent includes sodium bromide.

11. The effervescent tablet formulation of claim 3, wherein said hypochlorite releasing agent is selected from the group consisting of sodium dichloroisocyanurate, sodium trichloroisocyanurate, lithium hypochlorite, calcium hypochlorite, and magnesium hypochlorite.

12. A method for forming a disinfecting solution, comprising:
    preparing a first effervescent tablet comprising an effervescing agent and a bromide releasing agent;
    preparing a second effervescent tablet comprising an effervescing agent and a hypochlorite releasing agent;
    providing a lubricating agent in at least one of said tablets; and
    dissolving at least one of said first tablet and at least one of said second tablet in water to form a disinfecting solution.

13. The effervescent tablet formulation of claim 3, wherein said hypochlorite releasing agent includes sodium dichloroisocyanurate.

14. A disinfectant effervescent tablet formulation, comprising:
    a first tablet comprising an effervescing agent comprising a mixture of sodium bicarbonate and citric acid, a filler, sodium bromide, and a lubricating agent; and
    a second tablet comprising an effervescing agent comprising a mixture of sodium bicarbonate and citric acid, a filler, sodium dichloroisocyanurate, and lubricating agents.

15. The effervescent tablet formulation of claim 3, wherein said effervescent agent includes a mixture of sodium bicarbonate and citric acid.

* * * * *